United States Patent
Iijima

(10) Patent No.: US 9,638,814 B2
(45) Date of Patent: May 2, 2017

(54) RADIATION IMAGING APPARATUS, RADIATION IMAGING SYSTEM, AND STORAGE MEDIUM

(71) Applicant: CANON KABUSHIKI KAISHA, Tokyo (JP)

(72) Inventor: Tadahiko Iijima, Yokohama (JP)

(73) Assignee: CANON KABUSHIKI KAISHA, Toyko (JP)

( * ) Notice: Subject to any disclaimer, the term of this patent is extended or adjusted under 35 U.S.C. 154(b) by 106 days.

(21) Appl. No.: 14/218,094

(22) Filed: Mar. 18, 2014

(65) Prior Publication Data

US 2014/0295767 A1   Oct. 2, 2014

(30) Foreign Application Priority Data

Mar. 29, 2013  (JP) ................................ 2013-074863

(51) Int. Cl.
*G01T 7/00*  (2006.01)

(52) U.S. Cl.
CPC ...................................... *G01T 7/00* (2013.01)

(58) Field of Classification Search
CPC .......... G01T 7/00; H04B 1/005; H04B 1/401; H04B 5/00
USPC ......................... 455/41.1, 41.2, 78, 83, 552.1
See application file for complete search history.

(56) References Cited

U.S. PATENT DOCUMENTS

| | | | |
|---|---|---|---|
| 8,249,505 B1 * | 8/2012 | Goldner | H04W 48/18 455/41.2 |
| 8,675,624 B2 | 3/2014 | Tachikawa et al. | 378/114 |
| 9,160,985 B2 * | 10/2015 | Endo | H04N 7/185 |
| 2005/0272386 A1 | 12/2005 | Kawakami et al. | 455/151.2 |
| 2007/0178935 A1 * | 8/2007 | Shim | H04W 52/0235 455/552.1 |
| 2008/0298331 A1 | 12/2008 | Shimura | 370/338 |
| 2009/0034683 A1 | 2/2009 | Tamakoshi | 378/91 |
| 2009/0124284 A1 * | 5/2009 | Scherzer | H04M 1/72561 455/552.1 |
| 2011/0116486 A1 | 5/2011 | Tachikawa et al. | 370/338 |
| 2012/0075600 A1 | 3/2012 | Sato et al. | 355/18 |
| 2012/0106496 A1 | 5/2012 | Sakai | 370/329 |

(Continued)

FOREIGN PATENT DOCUMENTS

CN  101146480    3/2008
CN  101316208   12/2008

(Continued)

OTHER PUBLICATIONS

Office Action issued on Jan. 26, 2016 in counterpart application P.R. China patent application 201410124023.3, with translation.

*Primary Examiner* — Tuan Pham
(74) *Attorney, Agent, or Firm* — Fitzpatrick, Cella, Harper & Scinto

(57) ABSTRACT

A radiation imaging apparatus including a radiation detection unit in which a plurality of photoelectric conversion devices configured to convert radiation into electric charges are arranged and a communication unit configured to output image data formed from electric charges read out from the photoelectric conversion devices includes a setting unit configured to perform setting for connecting the communication unit wirelessly to an external apparatus, by executing processing based on a plurality of setting methods.

19 Claims, 10 Drawing Sheets

(56) References Cited

U.S. PATENT DOCUMENTS

| | | | |
|---|---|---|---|
| 2012/0151023 A1* | 6/2012 | Won | H04L 41/0806 709/222 |
| 2012/0163542 A1 | 6/2012 | Kitano et al. | 378/91 |
| 2012/0218918 A1 | 8/2012 | Takae et al. | 370/255 |
| 2012/0236975 A1 | 9/2012 | Yamagishi | 375/346 |
| 2013/0137377 A1 | 5/2013 | Endo et al. | 455/66.1 |

FOREIGN PATENT DOCUMENTS

| | | |
|---|---|---|
| CN | 102076119 | 5/2011 |
| CN | 102525493 | 7/2012 |
| JP | 2005-347911 | 12/2005 |
| JP | 2009-027639 | 2/2009 |
| JP | 2010-125275 | 6/2010 |
| JP | 2010-278536 | 12/2010 |
| JP | 2011-120885 | 6/2011 |
| JP | 2012-100796 | 5/2012 |
| JP | 2012-139258 | 7/2012 |
| JP | 2012-175614 | 9/2012 |
| JP | 2012-191586 | 10/2012 |
| KR | 10-2012-0036992 | 4/2012 |
| WO | WO 2012/017755 A | 2/2012 |

\* cited by examiner

RADIATION IMAGING APPARATUS, RADIATION IMAGING SYSTEM, AND STORAGE MEDIUM

BACKGROUND OF THE INVENTION

Field of the Invention

The present invention relates to a radiation imaging apparatus which acquires the intensity distribution of radiation transmitted through an object as an image, a radiation imaging system, and a storage medium.

Description of the Related Art

There has been commercially available a radiation imaging system using a radiation generating apparatus for irradiating an object with radiation, a radiation imaging apparatus for generating a clear radiation image by performing image processing for a radiation image obtained by digitizing a radiation image which is the intensity distribution of radiation, and an image processing apparatus. Such a radiation imaging system transfers, to the image processing apparatus such as a control computer for image processing and storage, radiation image data obtained by the radiation imaging apparatus upon causing the radiation generating apparatus to irradiate an object with radiation. The image processing apparatus displays an image having undergone image processing on a display device such as a display.

The radiation imaging apparatus is formed by stacking a scintillator on a photoelectric conversion device (conversion device) for converting radiation into an image signal electric charge (an electric signal), and the like. The radiation imaging apparatus converts radiation into visible light through the scintillator, holds the visible light as electric charges, and forms an image from the amount of readout electric charges.

Recently, as the above digitized radiation imaging apparatus, a wireless radiation imaging apparatus capable of wireless communication has been developed. The radiation imaging apparatus transfers an acquired image to a control computer for image processing and storage by using a wireless system based on the IEEE802.11 standard or the like. At this time, the wireless radiation imaging apparatus is connected to an access point to transmit data via the access point. Alternatively, the apparatus sometimes communicates data by temporarily forming a wireless group such as an ad-hoc or Wi-Fi Direct group without going through any access point. One wireless radiation imaging apparatus is sometimes used in a plurality of imaging rooms. Control computers are sometimes arranged in the respective imaging rooms to use the wireless radiation imaging apparatus upon switching between the control computers to be connected to the wireless radiation imaging apparatus. In this case, it is necessary to make wireless settings such as SSID (Service Set Identifier) or PSK (Pre-Shared Key) settings for connection to an access point to be connected to the radiation imaging apparatus and settings for connection to a system.

Japanese Patent Laid-Open No. 2011-120885 discloses a method of performing wireless setting by using near field communication different from an image transfer wireless scheme, as a method of designating a transmission destination in advance in a radiation imaging apparatus having no operation screen for setting an access point to be connected and a wireless group.

In addition, as a method of performing wireless setting, Japanese Patent Laid-Open No. 2012-191586 discloses a method of performing wireless setting upon cable connection. In addition, Japanese Patent Laid-Open No. 2010-278536 discloses a method of starting PBC (Push Button Configuration) operation in WPS (Wi-Fi Protected Setup) at the time of power activation.

However, the method of performing wireless setting by proximity wireless communication as disclosed in Japanese Patent Laid-Open No. 2011-120885 requires an apparatus and components for proximity wireless communication. This may increase the cost of a radiation imaging system. In addition, when using a device for performing proximity wireless communication upon connecting it to a control computer, forgetting to install the device for proximity wireless communication or losing it makes it impossible to perform wireless connection.

In addition, according to the method of performing wireless setting for cable connection as disclosed in Japanese Patent Laid-Open No. 2012-191586, since a radiation imaging apparatus and a cable are too heavy and large for the user to connect them with his/her hand, he/she is likely to connect the radiation imaging apparatus while placing it on a base. This requires a space to place the radiation imaging apparatus when performing connection.

Furthermore, in the method of starting PBC (Push Button Configuration) operation in WPS (Wi-Fi Protected Setup) at the time of power activation as disclosed in Japanese Patent Laid-Open No. 2010-278536, the user needs to temporarily turn off the power supply for wireless setting. Some radiation imaging apparatus is designed to make it difficult to disconnect the power supply to prevent the power supply from being accidentally disconnected at the time of imaging operation. Some method is designed to omit a power supply button and make it impossible to turn off the power supply without dismounting a battery. In this case, when connecting to another access point upon power activation, it is necessary to dismount the battery.

The present invention provides a radiation imaging technique capable of performing setting for connection to an external apparatus, by executing processing based on a plurality of setting methods.

SUMMARY OF THE INVENTION

According to one aspect of the present invention, there is provided a radiation imaging apparatus including a radiation detection unit in which a plurality of photoelectric conversion devices configured to convert radiation into electric charges are arranged and a communication unit configured to output image data formed from electric charges read out from the photoelectric conversion devices, the apparatus comprising: a setting unit configured to perform setting for connecting the communication unit wirelessly to an external apparatus, by executing processing based on a plurality of setting methods; and a selection unit configured to select one of the plurality of setting methods in accordance with an input from an operation unit.

According to another aspect of the present invention, there is provided a radiation imaging apparatus which wirelessly communicates with a relay apparatus for wireless communication, the apparatus comprising: a radiation detection unit; a battery configured to supply power to the radiation detection unit; a wireless communication circuit; a housing configured to accommodate the radiation detection unit, the battery, and the wireless communication circuit; a button arranged on a side surface of the housing; and a control unit configured to perform first control to control power supply from the battery in accordance with pressing of the button and second control to cause the wireless communication circuit to perform communication for performing wireless communication setting with the relay apparatus.

According to still another aspect of the present invention, there is provided a radiation imaging system including a radiation imaging apparatus including a radiation detection unit in which a plurality of photoelectric conversion devices configured to convert radiation into electric charges are arranged and a communication unit configured to output image data formed from electric charges read out from the photoelectric conversion devices, and an imaging control apparatus configured to control the radiation imaging apparatus, the radiation imaging apparatus comprising: a setting unit configured to perform setting for connecting the communication unit wirelessly to an external apparatus, by executing processing based on a plurality of setting methods; and a selection unit configured to select one of the plurality of setting methods in accordance with an input from an operation unit.

According to the present invention, it is possible to perform setting for connection to an external apparatus, by executing processing based on a plurality of setting methods.

For example, it is possible to select a method which facilitates performing setting for wireless connection to a radiation imaging apparatus in accordance with a setting environment or use state. In addition, even if it is not possible to perform a given wireless setting method due to some factor, it is possible to perform wireless setting by using an alternate method.

Further features of the present invention will become apparent from the following description of exemplary embodiments (with reference to the attached drawings).

DESCRIPTION OF THE EMBODIMENTS

Embodiments of the present invention will be exemplarily described in detail below with reference to the accompanying drawings. Note that the constituent elements described in the embodiments are merely examples. The technical scope of the present invention is determined by the scope of claims and is not limited by the following individual embodiments.

Figure 1:
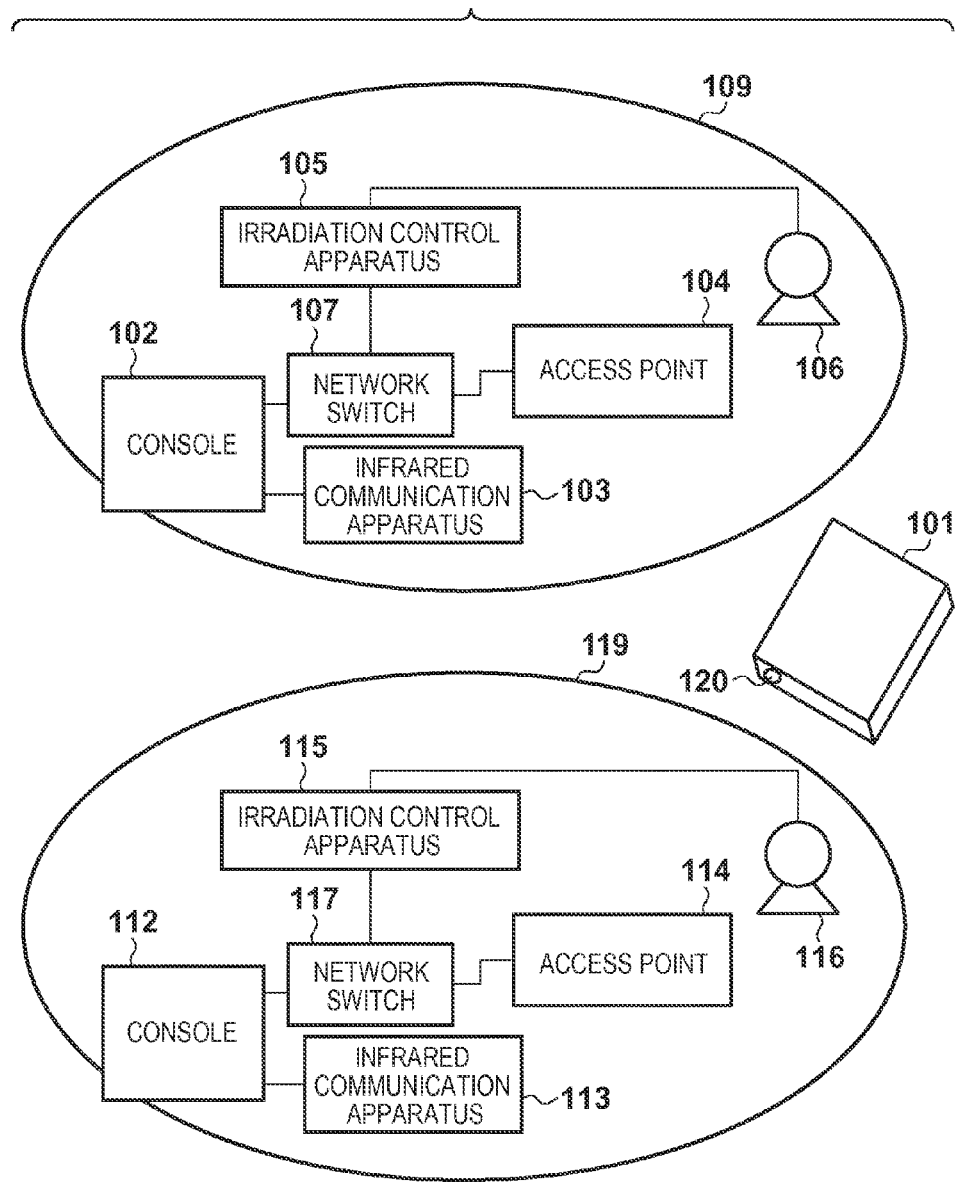
FIG. 1 is a view exemplarily showing the arrangement of a radiation imaging system according to an embodiment.

FIG. 1 is a view exemplarily showing the arrangement of a radiation imaging system according to an embodiment. A radiation imaging system 109 and a radiation imaging system 119 belong to different networks. When a radiation imaging apparatus 101 is connected to an access point 104 (wireless relay apparatus) by wireless setting, the radiation imaging apparatus 101 is used by the radiation imaging system 109. When the radiation imaging apparatus 101 is connected to an access point 114 (wireless relay apparatus) by wireless setting, the radiation imaging apparatus 101 is used by the radiation imaging system 119. Note that the two radiation imaging systems 109 and 119 are exemplarily shown as the arrangements of the radiation imaging systems shown in FIG. 1. However, the scope of this embodiment is not limited to this example and can be applied to an arrangement constituted by two or more radiation imaging systems.

Figure 11:
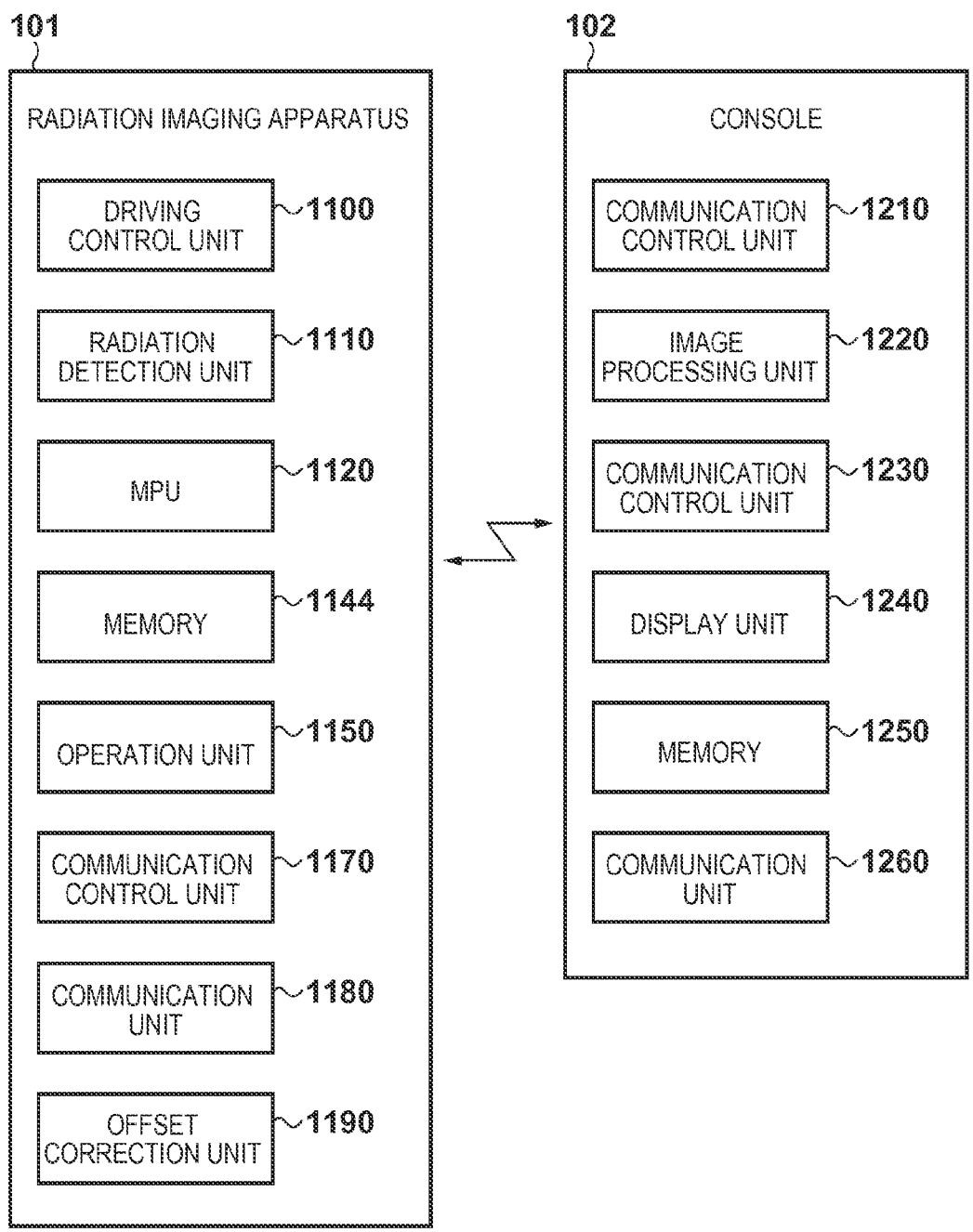
FIG. 11 is a block diagram for explaining the functional arrangements of a radiation imaging apparatus and console.

FIG. 11 is a block diagram for explaining the functional arrangements of the radiation imaging apparatus and console. Although FIG. 11 exemplarily shows the arrangement of a console 102 of the radiation imaging system 109 as the functional arrangement of the console, a console 112 of the radiation imaging system 119 has the same arrangement.

The radiation imaging apparatus 101 includes a driving control unit 1100, a radiation detection unit 1110, an MPU 1120, a memory 1140, an operation unit 1150, a communication control unit 1170, a communication unit 1180, and an offset correction unit 1190. A plurality of photoelectric conversion devices configured to convert radiation into electric charges are arranged in the radiation detection unit 1110. The radiation detection unit 1110 detects the radiation emitted from radiation generating apparatuses 106 and 116. For example, the radiation detection unit 1110 includes a sensor array having a two-dimensional array of pixels, each constituted by a conversion device which converts radiation into an image signal electric charge (electric signal) and a switch element such as a TFT which transfers an electric signal to the outside. The driving control unit 1100 drives the radiation detection unit 1110. The radiation detection unit 1110 controlled by the driving control unit 1100 outputs image data formed from electric charges read out from photoelectric conversion devices.

In addition, the radiation imaging apparatus 101 includes the communication control unit 1170 which controls communication with the console 102 (imaging control apparatus). The communication unit 1180 includes a wireless communication circuit for performing wireless communication between the radiation imaging apparatus 101 and the console and a wired communication circuit for performing wired communication between the radiation imaging apparatus 101 and the console. The communication control unit 1170 controls the operation of the wireless communication circuit and wired communication circuit under the control of the MPU 1120.

The memory 1140 functions as a work area for the MPU 1120 or a storage unit which stores the image captured by the radiation imaging apparatus 101. The memory 1140 stores firmware executed in processing by the MPU 1120. The firmware is read out and executed in accordance with processing by the MPU 1120.

The operation unit 1150 accepts the selection of a wireless setting method in accordance with an input via an operation input unit (for example, a button 120). It is possible to perform wireless setting for the radiation imaging apparatus 101 by a plurality of different wireless setting methods, as will be described later. The MPU 1120 can select which one of the plurality of wireless setting methods is to be used to perform wireless setting (communication setting), in accordance with an input from the operation unit 1150.

The offset correction unit 1190 performs the offset correction of subtracting offset image data acquired from only the dark electric charge components in the respective pixels from radiation image data to be described later with reference to FIG. 2.

In addition, the radiation imaging apparatus 101 includes a power control unit which controls a battery and power supply from the battery. The battery is an example of a power supply. The power control unit switches the supply of power to the radiation imaging apparatus 101 and turns on and off the apparatus in accordance with the pressing of the button 120. Having a battery makes the radiation imaging apparatus have high portability.

The respective units of the radiation imaging apparatus 101 are accommodated in a housing. For example, the button 120 is arranged on a side surface of the housing.

The control unit of the radiation imaging apparatus 101 performs different types of control, for example, power supply control (first control) and communication control (second control), in accordance with the pressing of the button 120. Upon detecting that the button is pressed once, the communication control unit of the control unit limits the supply of power to a portion to turn off the power supply when the power supply is on. Alternatively, the control unit may turn off the supply of power. When the power supply is off, in order to turn on the power supply, the control unit starts supplying power to a unit to which no power has been supplied. In this manner, the communication control unit implements ON/OFF control of the power supply. Upon detecting that the button 120 is consecutively pressed a plurality of times, the control unit causes the communication unit to start communication based on the WPS standard to perform wireless communication setting with respect to the access point 104 (relay apparatus). This makes it possible to wirelessly transmit radiation image data from the radiation imaging apparatus 101 and wirelessly perform synchronous communication with the radiation generating apparatus.

Executing different types of processing in accordance with the modes of operating the same button in this manner will decrease the sizes of the operation unit and its related circuits and components, resulting in contributing to a reduction in the size and weight of the portable radiation imaging apparatus.

The console 102 (imaging control apparatus) controls the operation state of the radiation imaging apparatus 101, and processes the radiation image data captured by the radiation imaging apparatus 101. The console 102 controls the radiation imaging apparatus 101 based on the operation of an external UI apparatus or the instruction generated by internal processing in the console 102. A communication control unit 1210 of the console 102 (imaging control apparatus) controls data communication between the radiation imaging apparatus 101 and the console 102, for example, communication for wireless setting with respect to the radiation imaging apparatus 101 and the reception of the image transferred from the radiation imaging apparatus 101.

A communication unit 1260 of the console 102 includes a wireless communication circuit for performing wireless communication between the radiation imaging apparatus 101 and the console 102 and a wired communication circuit for performing wired communication between the radiation imaging apparatus 101 and the console 102. The communication control unit 1210 controls the operation of the wireless communication circuit and wired communication circuit.

A memory 1250 of the console 102 functions as a storage unit which stores the image (captured image data) transmitted from the radiation imaging apparatus 101. In addition, the memory 1250 stores the firmware executed in processing by the console 102. For example, the firmware is read out and executed in accordance with processing by the communication control unit 1210 and an image processing unit 1220.

The image processing unit 1220 of the console 102 performs image processing for converting the captured image received from the radiation imaging apparatus 101 into an image suitable for diagnosis. A display control unit 1230 of the console 102 performs display control for displaying, on a display unit 1240, an image based on the electric charges read out from the radiation detection unit 1110, an operation UI, and the like based on the captured image data transmitted to the console 102. In addition, the display control unit 1230 displays a UI for wireless setting with respect to the radiation imaging apparatus 101 on the display unit 1240.

Referring back to FIG. 1, infrared communication apparatuses 103 and 114 transmit infrared reception data to the consoles 102 and 112, and transmit infrared in accordance with instructions from the consoles 102 and 112. Network switches 107 and 117 are line concentrators for Ethernet® communication. The radiation imaging apparatus 101 can perform communication in the infrastructure mode relaying the access points 104 and 114 (wireless relay apparatuses). The radiation imaging apparatus 101 has the button 120 for starting wireless setting. In addition, each access point has a WPS (Wi-Fi Protected Setup) PBC (Push Button Configuration) function. Pressing the switch on the main body of each of the access points 104 and 114 will execute processing based on the WPS PBC function.

Irradiation control apparatuses 105 and 115 communicate with the radiation imaging apparatus 101 and control radiation irradiation timings between the radiation generating apparatuses 106 and 116 and the radiation imaging apparatus 101. The radiation generating apparatuses 106 and 116 generate radiation in accordance with the timings controlled by the irradiation control apparatuses 105 and 115. The radiation imaging apparatus 101 performs imaging operation with the radiation emitted from one of the radiation generating apparatuses 106 and 116 in accordance with the irradiation start timing.

Figure 2:
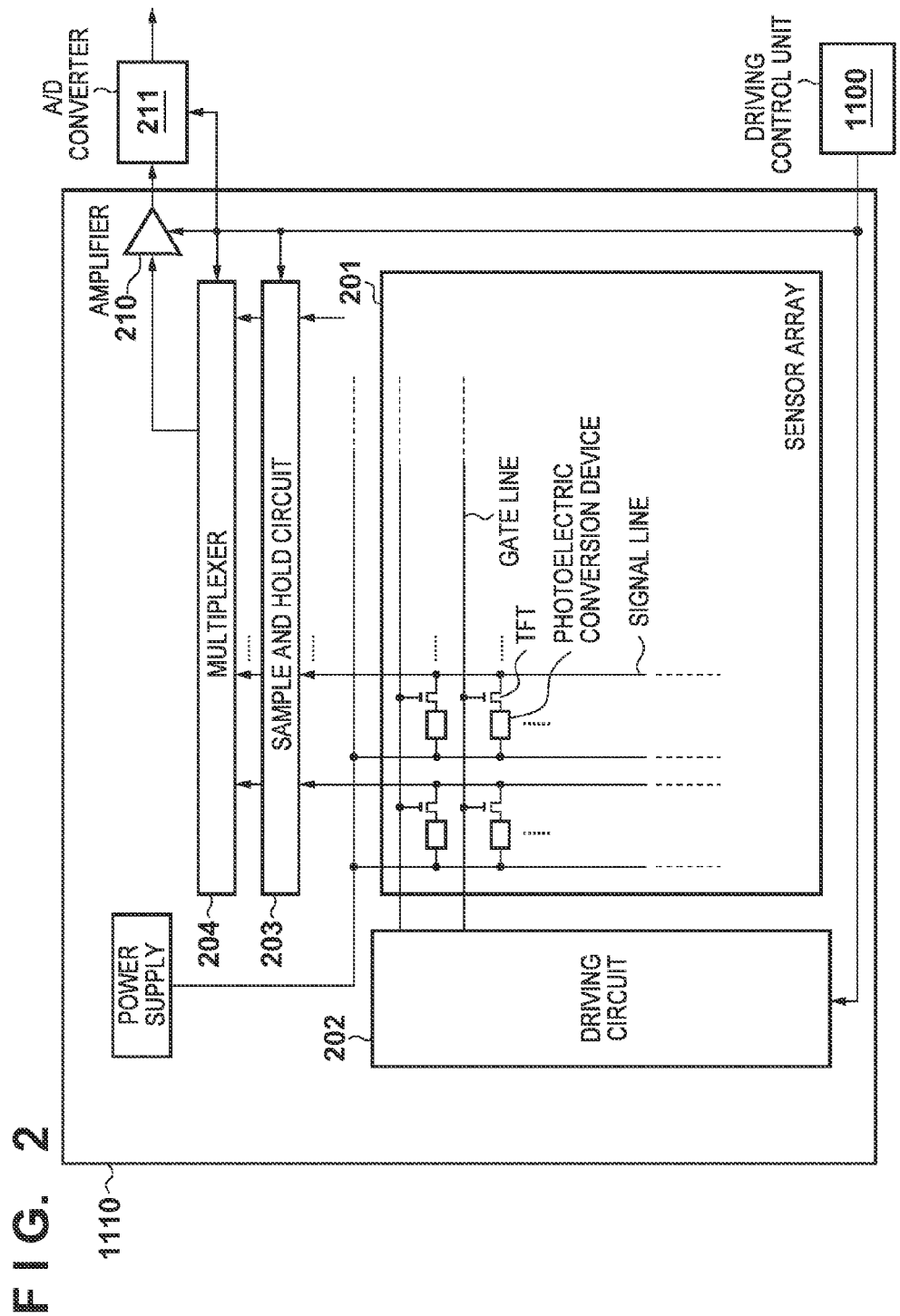
FIG. 2 is a block diagram showing an example of the arrangement of a radiation detection unit.

FIG. 2 is a circuit diagram showing an example of the arrangement of the radiation detection unit 1110. A drive circuit 202 simultaneously addresses all the pixels on the rows on a sensor array 201, which are two-dimensionally arranged. After that, electric charges (pixel outputs) of the respective pixels held by a sample and hold circuit 203 are sequentially read out via a multiplexer 204 and amplified by an amplifier 210. An A/D converter 211 converts the resultant electric charges into digital image data. Every time scanning on each row is complete, the drive circuit 202 sequentially drives and scans the respective subsequent rows on the sensor array 201 to finally convert the electric charges output from all the pixels into digital values. This makes it possible to read out the radiation image data. In this case, the apparatus performs scanning while a voltage applied to each column signal line connected to a corresponding one of the pixels on each row is fixed to a specific value, and discards obtained electric charges to discharge dark electric charges, thereby discharging (resetting) the dark electric charges accumulated in the respective pixels. This completes the initialization of the sensor array 201. A driving control unit 220 controls driving of the radiation detection unit 1110, a readout operation, and the like.

If the image data converted by the A/D converter 211 is radiation image data obtained by radiation irradiation, offset correction is performed to subtract, from the radiation image data, offset image data obtained from only the dark electric charge components in the respective pixels. By performing offset correction, it is possible to obtain a captured image from which unnecessary dark electric charge components have been removed.

Figure 3:
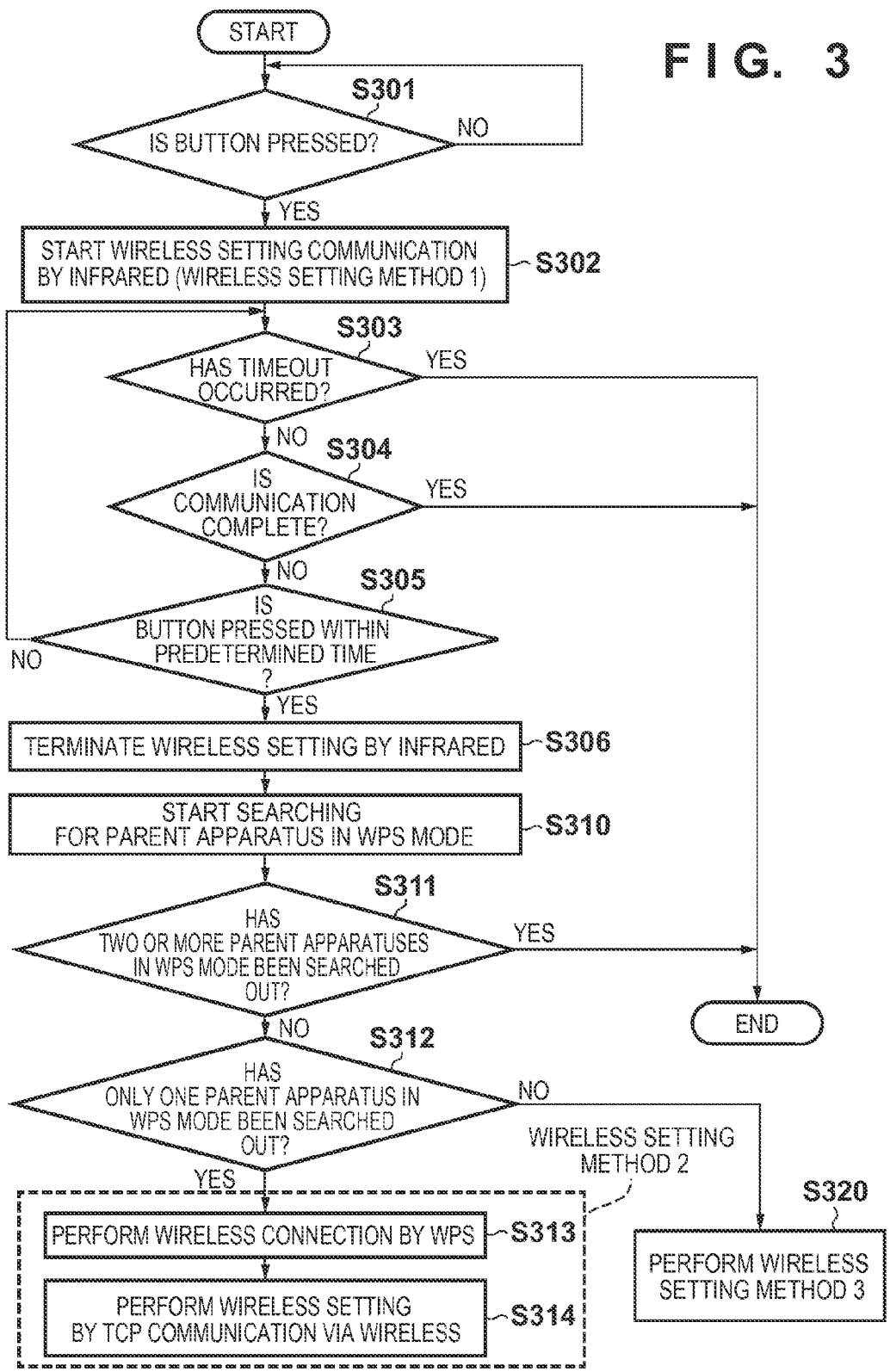
FIG. 3 is a flowchart for explaining processing in a radiation imaging apparatus according to the embodiment.

FIG. 3 is a flowchart for explaining a procedure for processing in the radiation imaging apparatus 101 according to the embodiment. In step S301, the MPU 1120 of the radiation imaging apparatus 101 determines whether it has detected the pressing of the button 120. Upon not detecting the pressing of the button 120 (NO in step S301), the MPU 1120 sets a standby state. Upon detecting the pressing of the button 120 (YES in step S301), the MPU 1120 starts communication for wireless setting by infrared (wireless setting method 1) in step S302. Wireless settings in this case include not only settings for communication with an access point but also setting information of information necessary to construct a radiation imaging system. For example, the wireless settings include setting information of information necessary to construct a radiation imaging system, such as the individual identification number (identification information) of the radiation imaging apparatus 101, the network address of the radiation imaging apparatus 101, and the network address of an irradiation control apparatus.

(Wireless Setting Method 1)

Figure 6:
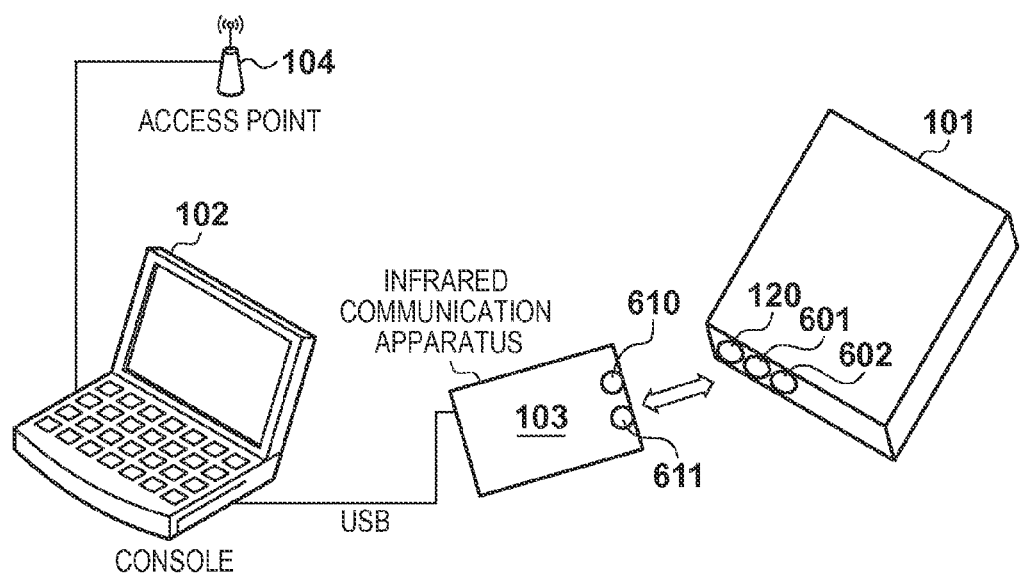
FIG. 6 is a perspective view for explaining processing based on wireless setting method 1.
Figure 8:
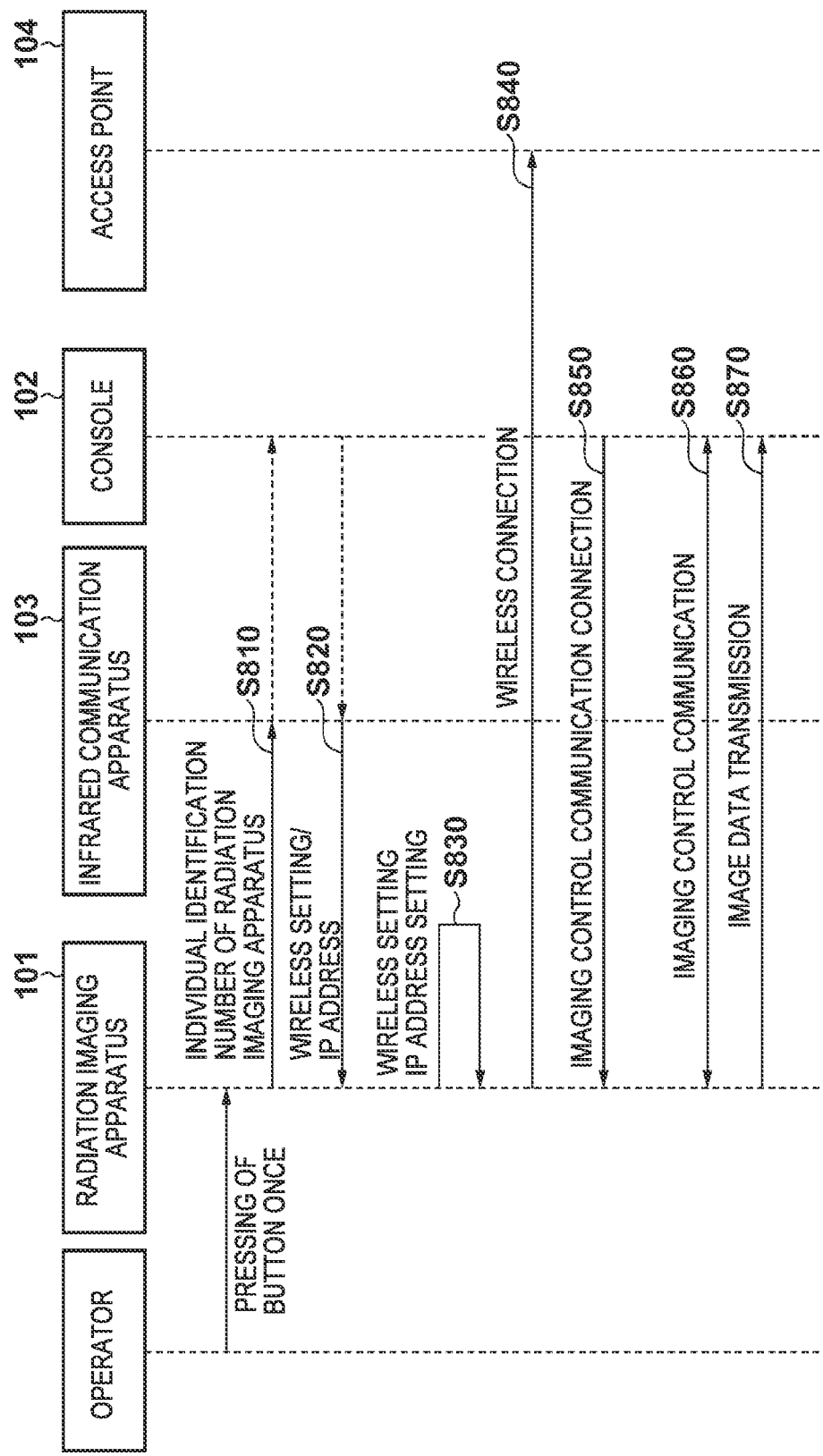
FIG. 8 is a chart for explaining processing based on wireless setting method 1.

FIGS. 6 and 8 are views for explaining processing for wireless setting by infrared (wireless setting method 1). The console 102 is connected to an infrared communication apparatus 103 via a USB (Universal Serial Bus). When an infrared receiving unit 610 receives infrared, the infrared communication apparatus 103 converts a received light pattern into reception data. The infrared communication apparatus 103 converts the reception data into data complying with the USB communication protocol and transmits the data to the console 102 via the USB. Upon receiving data (transmission data) transmitted from the console 102 by infrared based on the USB communication protocol, the infrared communication apparatus 103 causes an infrared emitting unit 611 to emit light in accordance with the transmission data.

When the user presses the button 120 of the radiation imaging apparatus 101, the MPU 1120 turns on the power supplies of an infrared emitting unit 601 and an infrared receiving unit 602 (power ON). The MPU 1120 of the radiation imaging apparatus 101 causes the infrared emitting unit 601 to emit light in accordance with data to be transmitted to the infrared communication apparatus 103. The infrared receiving unit 610 of the infrared communication apparatus 103 receives the infrared emitted by the infrared emitting unit 601.

When the infrared receiving unit 602 of the radiation imaging apparatus 101 receives the infrared emitted by the infrared emitting unit 611 of the infrared communication apparatus 103, the MPU 1120 converts the received light pattern into data.

In a sequence in wireless setting method 1 using infrared, upon detecting that the user has pressed the button 120, the MPU 1120 causes the infrared emitting unit 601 to emit light to transmit the individual identification number (identification information) of the radiation imaging apparatus 101.

The MPU 1120 controls the infrared emitting unit 601 so as to repeat the transmission of the individual identification number of the radiation imaging apparatus at predetermined time intervals until the infrared receiving unit 602 receives an ACK signal indicating that the infrared communication apparatus 103 has received the individual identification number of the radiation imaging apparatus (step S810).

When the infrared communication apparatus 103 receives the individual identification number (identification information) of the radiation imaging apparatus 101, the communication control unit 1210 of the console 102 analyzes the individual identification number (identification information). The console 102 generates information for enabling the radiation imaging apparatus 101 to connect to the radiation imaging system. The console 102 generates an IP address allocated to the radiation imaging apparatus, an SSID (Service Set Identifier) for connection to an access point, a PSK (Pre-Shared key), and the like in accordance with the individual identification number of the radiation imaging apparatus. The console 102 then transmits the generated information to the radiation imaging apparatus 101 via the infrared communication apparatus 103 (step S820).

Upon completion of the communication of the information for connection to the radiation imaging system by the infrared receiving unit 602 of the radiation imaging apparatus 101, wireless setting by infrared (wireless setting method 1) is complete.

The MPU 1120 of the radiation imaging apparatus 101 reflects the wireless settings and the IP address designated by the wireless setting method using infrared and performs wireless connection setting with respect to an access point via the communication control unit 1170 (step S830). Upon completion of the setting, the radiation imaging apparatus is wirelessly connected to the access point (step S840), establishes communication connection for imaging control in accordance with an instruction from the console (step S850), and performs imaging control communication (step S860). The radiation imaging apparatus 101 is connected to the radiation imaging system 109. This enables the radiation imaging apparatus 101 to wirelessly communicate with apparatuses (for example, the console 102 (imaging control apparatus) and the irradiation control apparatus 105) included in the radiation imaging system 109. In response to the reception of a signal from the console 102, the radiation imaging apparatus 101 performs driving operation for periodically resetting electric charges from photoelectric conversion devices via TFTs and starts driving operation for stabilizing the characteristics of the sensor. In addition, the radiation imaging apparatus 101 receives a signal for requesting the permission of radiation irradiation from the radiation generating apparatus 106 via the irradiation control apparatus. In accordance with this signal, the radiation imaging apparatus 101 repeats the above reset driving a predetermined number of times, and then turns off the TFTs on all the lines of a sensor array 201 to make transition to an electric charge accumulation state. In accordance with the transition to the accumulation state, the radiation imaging apparatus 101 transmits a signal for permitting radiation irradiation to the radiation generating apparatus 106 via the irradiation control apparatus 105. This causes the radiation generating apparatus 106 to emit radiation.

The communication control unit 1170 of the radiation imaging apparatus 101 wirelessly transmits the image data (radiation image data) captured by imaging control to the console (S870).

Infrared has directivity and contains a small amount of information for connection to the radiation imaging system. For this reason, when the user intentionally starts wireless connection setting, the radiation imaging apparatus 101 and the infrared communication apparatus 103 face each other in a positional relationship that enables communication. Therefore, the radiation imaging apparatus 101 and the infrared communication apparatus 103 complete communication in about several hundred msec. If communication is not complete in several sec, it indicates that the user has accidentally pressed the button 120 without any intention to perform wireless connection setting. Therefore, a communication timeout may be determined to complete the processing after the elapse of a predetermined time (for example, about 3 sec).

Referring back to FIG. 3, in step S303, the MPU 1120 determines whether a predetermined time (for example, about 3 sec) has elapsed without completion of communication by wireless setting method 1. If the predetermined time has elapsed without completion of communication (YES in step S303), the MPU 1120 determines a timeout and terminates the processing.

If the MPU 1120 determines in step S303 that no timeout has occurred (NO in step S303), the process advances to step S304, in which the MPU 1120 determines whether communication by wireless setting method 1 is complete. If the infrared receiving unit 602 has completed reception of information for connection to the radiation imaging system, the MPU 1120 determines that communication for wireless setting by infrared (wireless setting method 1) is complete (YES in step S304), and terminates the processing. This completes the wireless setting processing by the radiation imaging apparatus 101 using wireless setting method 1.

On the other hand, if the MPU 1120 determines in step S304 that communication by wireless setting method 1 is not complete (NO in step S304), the process advances to step S305. Since infrared has directivity, if the radiation imaging apparatus 101 and the infrared communication apparatus 103 face each other in a place where they can communication with each other, they perform wireless setting by infrared and quickly complete wireless communication. Since the timeout time in wireless setting method 1 is as short as, for example, 3 sec, even if the user accidentally presses the button 120 once, a timeout occurs after the elapse of 3 sec, and the original state is restored.

In step S305, the MPU 1120 determines whether it has detected the pressing of the button 120 again within a predetermined time after the detection of the pressing of the button 120 in step S301. If the MPU 1120 has not detected the pressing of the button 120 again within the predetermined time (NO in step S305), the process returns to step S303 to repeat the same processing. If the MPU 1120 determines in step S305 that it has detected the pressing of the button 120 again within the predetermined time, for example, 400 msec (YES in step S305), the process advances to step S306, in which the MPU 1120 stops processing in wireless setting method 1 (step S306), and starts searching for a parent apparatus in the WPS mode (access point) (step S310).

If the MPU 1120 detects two or more access points set in the WPS mode in step S311 (YES in step S311), the MPU 1120 terminates the processing because it cannot discriminate which access point to connect to. If the MPU 1120 detects less than two access points in the WPS mode (NO in step S311), the process advance to step S312.

Upon detecting one access point set in the WPS mode in step S312 (YES in step S312), the MPU 1120 performs wireless setting in the WPS mode (step S313) to establish wireless communication. Subsequently, the MPU 1120 performs wireless setting including setting information necessary for the construction of this system by wireless communication as in wireless setting method 1 (step S314). The processes in steps S313 and S314 will be collectively referred to as wireless setting method 2. The MPU 1120 reflects the wireless settings and IP address designated by the console using wireless setting method 2 in the radiation imaging apparatus 101 to perform setting for wireless connection to an access point via the communication control unit 1170.

Upon detecting an access point in the WPS mode in determination in step S312, the MPU 1120 starts wireless setting method 3 (step S320). Wireless setting method 3 will be described later.

(Wireless Setting Method 2)

Figure 7:
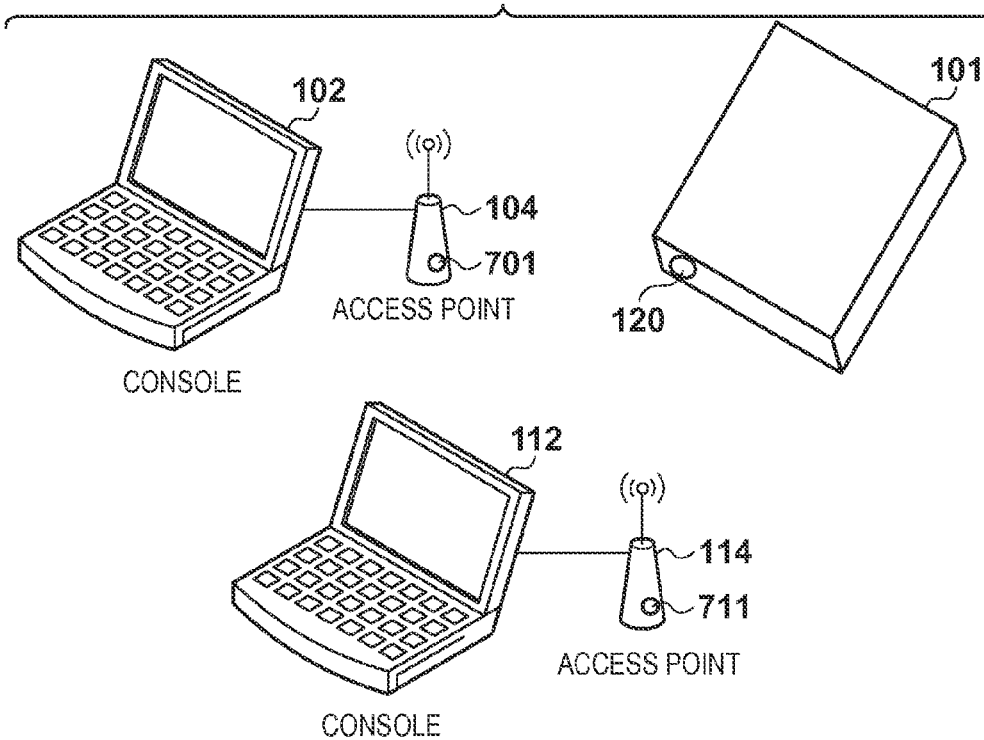
FIG. 7 is a perspective view for explaining processing based on wireless setting method 2.
Figure 9:
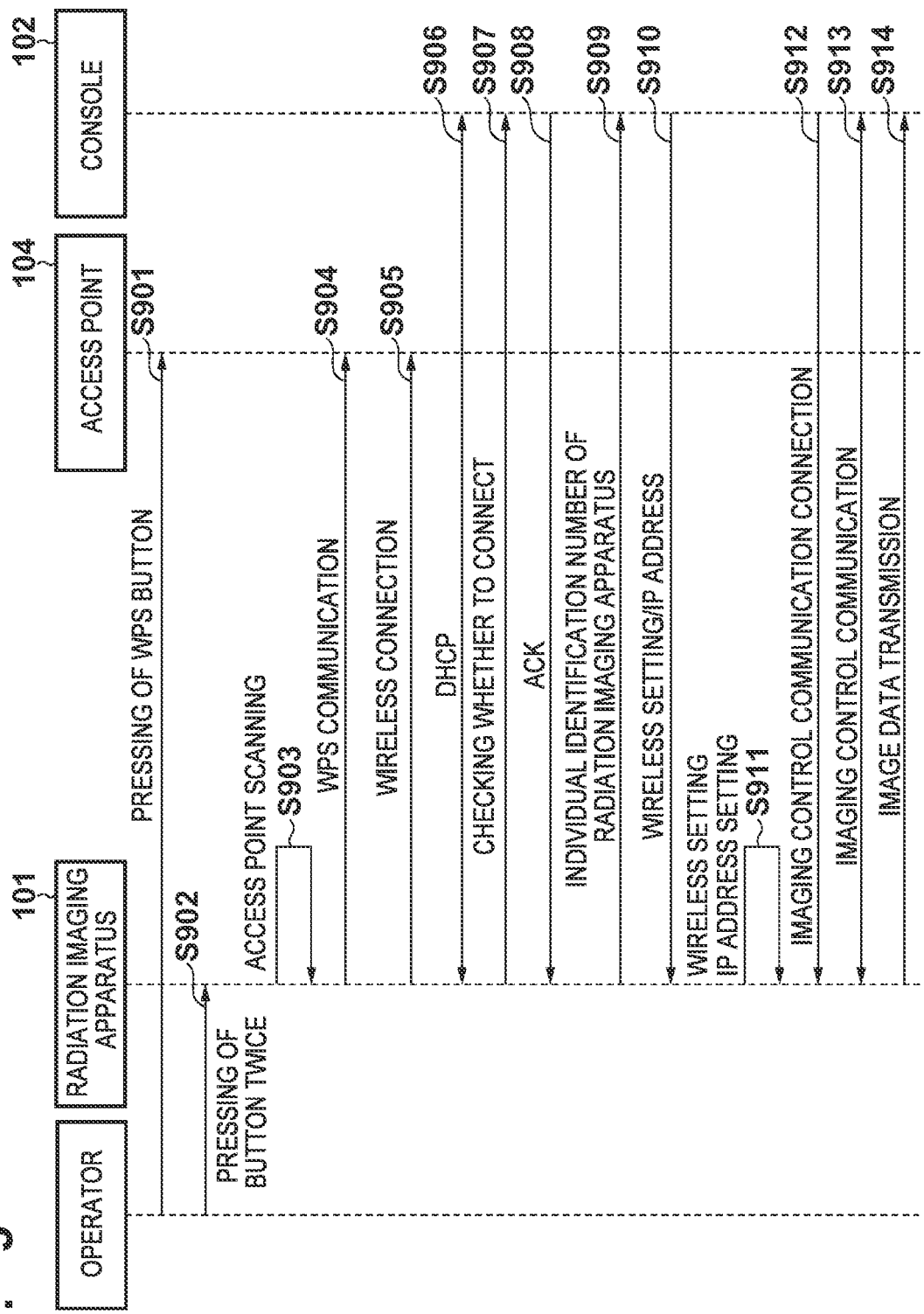
FIG. 9 is a chart for explaining processing based on wireless setting method 2.

FIGS. 7 and 9 are views for explaining wireless setting method 2. The access points 104 and 114 have the WPS (Wi-Fi Protected Setup) function, and includes WPS buttons 701 and 711 for starting the PBC (Push Button Configuration) function. First of all, the user presses the WPS button 701 of the access point 104 to which he/she wants to connect the radiation imaging apparatus 101 (step S901). The access point 104 is set in the WPS mode for a predetermined time after the pressing of the WPS button 701, for example, about 60 sec. The user then consecutively presses the button 120 of the radiation imaging apparatus 101 a plurality of times (for example, two times consecutively) (step S902). This makes the MPU 1120 of the radiation imaging apparatus 101 start searching for a parent apparatus in the WPS mode. The MPU 1120 then performs wireless setting in accordance with the WPS protocol and is connected to an access point in the WPS mode (the access point 104 in this case) (step S904). This establishes WPS communication between the radiation imaging apparatus 101 and the access point 104 (step S905).

In the console 102, the DHCP sever is operating and allocates an IP address to the radiation imaging apparatus 101 (step S906).

The radiation imaging apparatus 101 then requests a response to obtain a connection acknowledgment with respect to the console 102 (step S907), and waits for a response indicating the intention of connection (step S908). Note that the process can also advance from step S906 to step S909 without performing the processing in steps S907 and S908.

Subsequently, the MPU 1120 of the radiation imaging apparatus 101 transmits the individual identification number (identification information) of the radiation imaging apparatus 101 to the console 102 (step S909). The console 102 generates information necessary for the construction of this system, for example, an IP address allocated to the radiation imaging apparatus, SSID and PSK for connection to the access point 104, and the IP address of the irradiation control apparatus, in accordance with the individual identification number of the radiation imaging apparatus 101. The communication control unit 1210 of the console 102 then transmits the generated information to the radiation imaging apparatus 101 (step S910).

The MPU 1120 of the radiation imaging apparatus 101 performs wireless connection setting with the wireless settings and IP address designated by the console 102 being reflected in the radiation imaging apparatus 101 (step S911). Upon completion of setting, the radiation imaging apparatus 101 is wirelessly connected to the 102, establishes communication connection for performing imaging control (step S912), and performs imaging control communication (step S913).

The radiation imaging apparatus 101 is connected to the radiation imaging system 109, and can wirelessly communicate with apparatuses (for example, the console 102 (imaging control apparatus) and the irradiation control apparatus 105) included in the radiation imaging system 109. In response to the reception of a signal from the console 102, the radiation imaging apparatus 101 performs driving operation for periodically resetting electric charges from photoelectric conversion devices via TFTs and starts driving operation for stabilizing the characteristics of the sensor. In addition, the radiation imaging apparatus 101 receives a signal for requesting the permission of radiation irradiation from the radiation generating apparatus via the irradiation control apparatus 105. In accordance with this signal, the radiation imaging apparatus 101 repeats the above reset driving a predetermined number of times, and then turns off the TFTs on all the lines of the sensor array 201 to make transition to an electric charge accumulation state. In accordance with the transition to the accumulation state, the radiation imaging apparatus 101 transmits a signal for permitting radiation irradiation to the radiation generating apparatus 106 via the irradiation control apparatus 105. This causes the radiation generating apparatus 106 to emit radiation.

The communication control unit 1170 of the radiation imaging apparatus 101 wirelessly transmits image data (radiation image data) captured by imaging control to the console 102 (step S914).

(Wireless Setting Method 3)

Processing by wireless setting method 3 will be described next with reference to FIGS. 4 and 5. The display control units 1230 of the consoles 102 and 112 display user interfaces (connection buttons 410 and 411) for starting communication by wireless setting method 3 on the display units 1240 of the consoles 102 and 112. In addition, at the time of system installation, SSIDs (Service Set Identifiers) are set for access points which can be connected to the radiation imaging apparatus 101 by combining the common character string (common portion) of the SSID of the radiation imaging apparatus and character strings other than the common character string. This common character string (common portion) is used to search for an access point.

Figure 4:
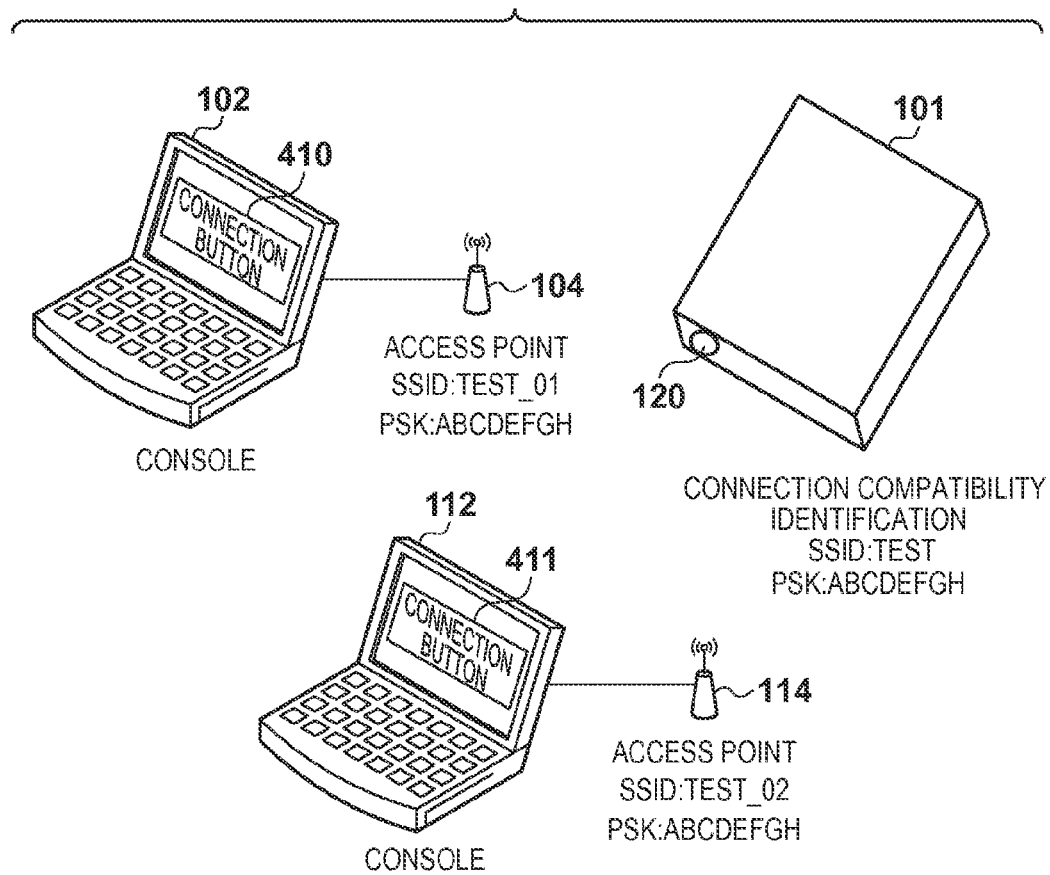
FIG. 4 is a perspective view for explaining processing based on wireless setting method 3.

FIG. 4 shows TEST_01 exemplarily set as the SSID of the access point 104 and TEST_02 exemplarily set as the SSID of the access point 114. The common character string for a search is "TEST", and "_01" and "_02" are respectively set as individual identification numbers for the access points 104 and 114. PSKs to be set for the respective access points are common to all the access points or data strings obtained from the SSIDs by a specific hash function. In this case, as an example of a PSK, a common character string "ABCDEFGH" is set. The stealth function is off for each access point.

In addition, in the radiation imaging apparatus 101, a character string (SSID) for which this system searches to identify a connection target is set to "TEST", and PSK is set to "ABCDEFGH". If the PSK set in an access point is obtained by a hash function, the hash function is registered in the radiation imaging apparatus 101 or the hash function set in the radiation imaging apparatus 101 is used.

In the environment set in the above manner, the user presses the connection button displayed on the display unit 1240 of the console of the system to which he/she wants to connect. Pressing the button 120 of the radiation imaging apparatus 101 after pressing the connection button can perform wireless setting for access points and the radiation imaging apparatus 101 by wireless setting method 3.

Figure 5:
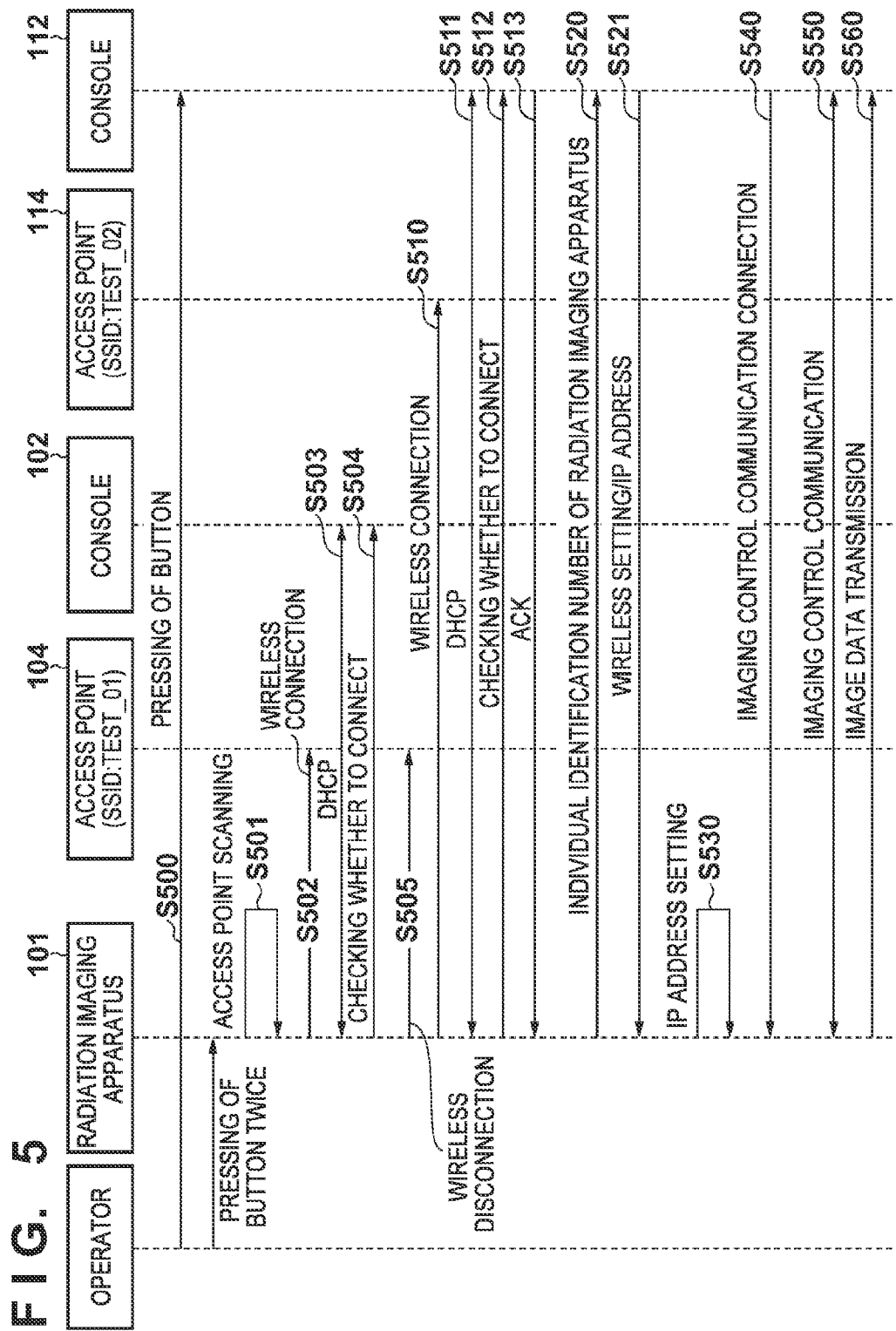
FIG. 5 is a chart for explaining processing based on wireless setting method 3.

FIG. 5 is a view for exemplarily explaining wireless setting for access points and the radiation imaging apparatus 101 by wireless setting method 3. First of all, the operator presses the connection button 411 of the console 112 (step S500). The operator then presses the button 120 of the radiation imaging apparatus 101 a plurality of times (for example, twice). Pressing the button 120 twice is determined when the pressing of the button 120 is detected within a predetermined time after the pressing of the button 120 is detected in determination processing in steps S301 and S305 of FIG. 3.

The MPU 1120 of the radiation imaging apparatus 101 stops the processing in wireless setting method 1, and starts searching for (scanning) a parent apparatus (access point) in the WPS mode (step S501). The MPU 1120 of the radiation imaging apparatus 101 searches for an access point having an SSID including "TEST" as a character string for identifying the access point as a connection target set in advance. If the MPU 1120 of the radiation imaging apparatus 101 has searched out a plurality of access points, the MPU 1120 sorts the access points in descending order of radio intensity (priority order setting). If the number of found access points exceeds a predetermined number, for example, five, or some access points exhibit radio intensities equal to or lower than a predetermined radio intensity, for example, −60 dB, the excess access points or the access points with radio intensities equal to or lower than the predetermined radio intensity are excluded from the next processing. This makes it possible to suppress the timeout time in wireless setting method 3 to a predetermined time or less. In this case, assume that two access points, namely the access points 104 and 114, are set as targets for connection in descending order of radio intensity.

The MPU 1120 sequentially performs wireless connection to the access points set as targets for connection in the above processing. First of all, the MPU 1120 of the radiation imaging apparatus 101 performs wireless connection to the access point 104 with the first priority, which exhibits the highest radio intensity (step S502). In the console 102, the DHCP server is operating and allocates an IP address to the radiation imaging apparatus 101 (step S503).

The radiation imaging apparatus 101 then outputs a request signal for a connection acknowledgment to the console 102 (step S504). In the case shown in FIG. 4, since the user has not pressed the connection button 410 of the console 102, the console 102 does not return a response indicating the intention of connection to the radiation imaging apparatus 101, and timeout occurs. The MPU 1120 then disconnects the wireless connection to the access point 104 (step S505).

The MPU 1120 is then wirelessly connected to the access point 114 with the second highest radio intensity (step S510). In the console 112, the DHCP server is operating and allocates an IP address to the radiation imaging apparatus 101 (step S511).

The radiation imaging apparatus 101 transmits a request for a connection acknowledgment to the console 112 (step S512). In accordance with this connection acknowledgment, the communication control unit 1210 of the console 112 transmits an ACK command (response signal) indicating the pressing of the connection button 411 to the radiation imaging apparatus 101 (step S513).

The MPU 1120 of the radiation imaging apparatus 101 transmits the individual identification number (identification information) of the radiation imaging apparatus 101 to the console 112 in response to the reception of an ACK command (response signal) (step S520).

The console 112 generates information necessary to the construction of this system. That is, in accordance with the individual identification number of the radiation imaging apparatus 101, the console 112 generates an IP address allocated to the radiation imaging apparatus, an SSID and PSK for connection to the access point 104, the IP address of the irradiation control apparatus, and the like. The communication control unit 1210 of the console 102 transmits the generated information to the radiation imaging apparatus 101 (step S521).

The MPU 1120 of the radiation imaging apparatus 101 performs wireless connection setting with the wireless settings and IP address designated by the console 112 being reflected in the radiation imaging apparatus 101 (step S530). Upon completion of setting, the radiation imaging apparatus 101 is wirelessly connected to the console 112, establishes communication connection for imaging control in accordance with an instruction from the console 102 (step S540), and performs imaging control communication (step S550). The radiation imaging apparatus 101 is connected to the radiation imaging system 119 and can wirelessly communicate with apparatuses (for example, the console 112 (imaging control apparatus) and the irradiation control apparatus 115) included in the radiation imaging system 119.

In response to the reception of a signal from the console 112, the radiation imaging apparatus 101 performs driving operation for periodically resetting electric charges from photoelectric conversion devices via TFTs and starts driving operation for stabilizing the characteristics of the sensor. In addition, the radiation imaging apparatus 101 receives a signal for requesting the permission of radiation irradiation from the radiation generating apparatus 116 via the irradiation control apparatus 115. In accordance with this signal, the radiation imaging apparatus 101 repeats the above reset driving a predetermined number of times, and then turns off the TFTs on all the lines of the sensor array 201 to make transition to an electric charge accumulation state. In accordance with the transition to the accumulation state, the radiation imaging apparatus 101 transmits a signal for permitting radiation irradiation to the radiation generating apparatus 116 via the irradiation control apparatus 115. This causes the radiation generating apparatus 116 to emit radiation.

The communication control unit 1170 of the radiation imaging apparatus 101 wirelessly transmits the image data (radiation image data) captured by imaging control to the console 112 (step S560). Radiation setting method 3 is an effective method as a wireless setting method which can be used even if an infrared communication apparatus or a WPS incompatible access point is used.

Second Embodiment

The first embodiment has exemplified the wireless setting sequentially using wireless setting method 1, wireless setting method 2, and wireless setting method 3. However, it is possible to simultaneously use wireless setting method 1, wireless setting method 2, and wireless setting method 3. For example, upon detecting the pressing of a button 120 once, an MPU 1120 of a radiation imaging apparatus 101 simultaneously executes wireless setting (wireless setting method 1) using infrared, wireless setting method 2 using WPS, and wireless setting method 3 using an SSID. The MPU 1120 of the radiation imaging apparatus 101 performs wireless setting by using a wireless setting method (one wireless setting method) of executed wireless setting method 1, wireless setting method 2, and wireless setting method 3 which has established communication first, and stops the processing in wireless setting methods except for one of the plurality of setting methods. If, for example, wireless setting method 1 has established communication first, the MPU 1120 stops the processing in wireless setting method 2 and wireless setting method 3.

Third Embodiment

Figure 10:
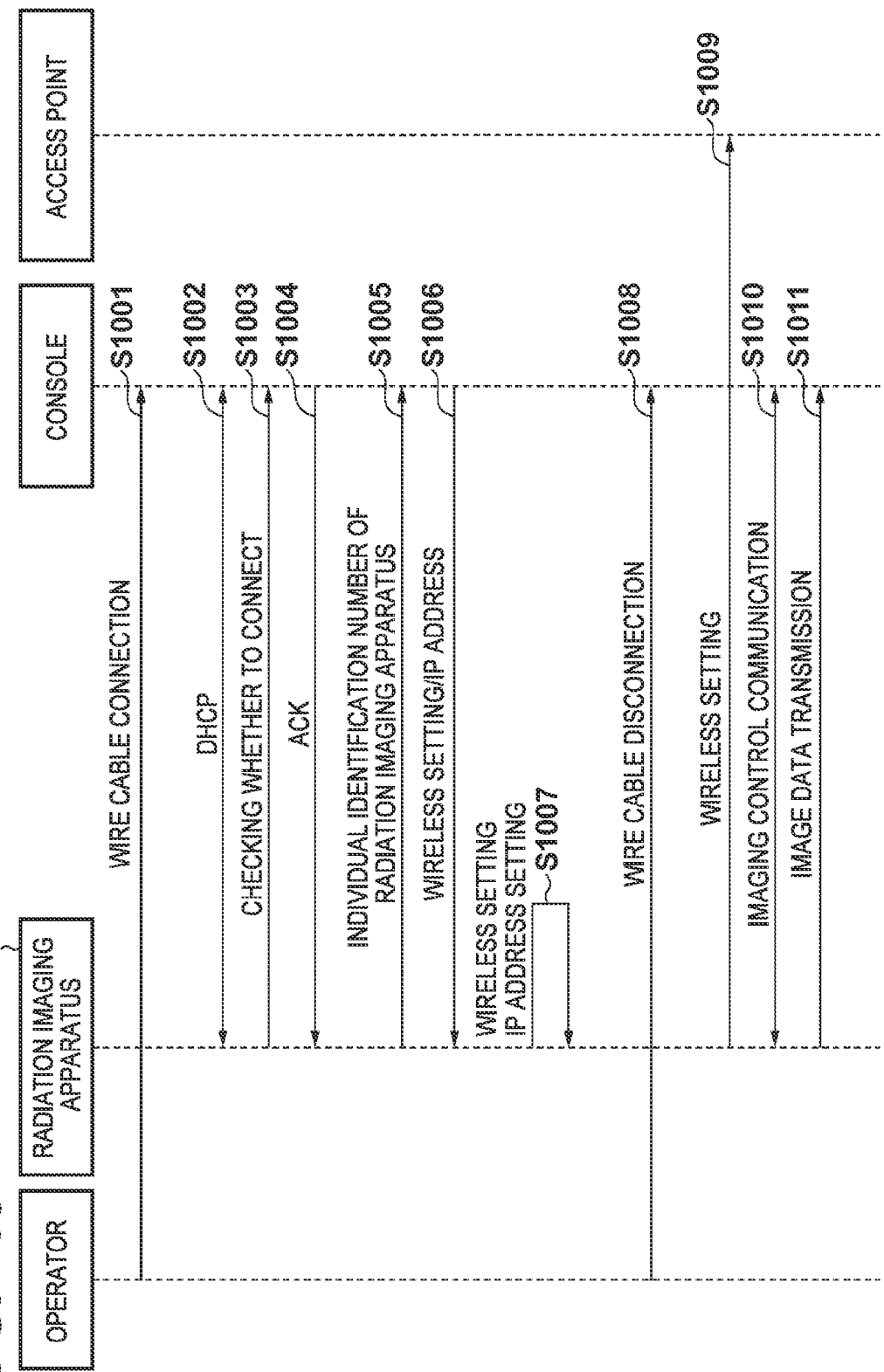
FIG. 10 is a chart for explaining a wireless setting method using wired communication.

This embodiment will exemplify an arrangement in which a console is wire-connected to a radiation imaging apparatus 101 to perform wireless setting in wire connection. FIG. 10 is a view showing a processing sequence for performing wireless setting by wire-connecting a console to a radiation imaging apparatus.

First of all, the operator connects the radiation imaging apparatus 101 to a desired console via a cable capable of Ethernet® communication (step S1001). For example, the radiation imaging apparatus 101 is connected to a console via a connector which can be connected to the apparatus and a dedicated cable having an RJ 45 connector. Note, however, that the radiation imaging apparatus 101 may be relayed to the console via another device as long as it is possible to perform Ethernet® communication. Connecting a wire cable enables the radiation imaging apparatus 101 and the console to perform Ethernet® communication.

In the console, the DHCP server is operating and allocates an IP address to a radiation imaging apparatus (step S1002).

The radiation imaging apparatus 101 then outputs a request signal for a connection acknowledgment to the console (step S1003). In accordance with this connection acknowledgment, a communication control unit 1210 of the console transmits an ACK command (response signal) representing a connection acknowledgment result to the radiation imaging apparatus 101 (step S1004). Note that the process can advance from step S1002 to step S1005 (to be described later) without performing the processing in steps S1003 and S1004.

The MPU 1120 of the radiation imaging apparatus 101 then transmits the individual identification number (identification information) of the radiation imaging apparatus 101 to the console (step S1005).

The console 102 generates an IP address allocated to the radiation imaging apparatus, SSID and PSK for connection to an access point 104, and the IP address of an irradiation control apparatus, in accordance with the individual identification number of the radiation imaging apparatus 101. The communication control unit 1210 of the console 102 then transmits the generated information to the radiation imaging apparatus 101 (step S1006).

The MPU 1120 of the radiation imaging apparatus 101 performs wireless connection setting with the wireless settings and IP address designated by the console being reflected in the radiation imaging apparatus 101 (step S1007).

Subsequently, the operator detaches the wire cable connecting the radiation imaging apparatus 101 to the console (step S1008). The MPU 1120 of the radiation imaging apparatus 101 then is wirelessly connected to an access point based on set wireless settings (step S1009), establishes communication connection for imaging control in accordance with an instruction from the console, and performs imaging control communication (step S1010). The contents of imaging control communication are the same as those in steps S550, S860, and S913 described above. An imaging control unit 117 of the radiation imaging apparatus 101 wirelessly transmits the image data (radiation image data) captured by imaging control to the console (step S1011).

Note that FIG. 10 shows a case in which when the operator detaches the wire cable (step S1008), the radiation imaging apparatus is wirelessly connected to the access point. However, when wireless setting is complete in step S1007, the radiation imaging apparatus may be wirelessly connected to the access point. When it is possible to perform wireless communication, the apparatus may simultaneously perform wireless communication and wired communication or may exclusively perform only one of the communications.

According to each embodiment described above, it is possible to perform setting for connection to a network by executing processing based on a plurality of setting methods. For example, it is possible to select a method which facilitates making settings for wireless connection to a radiation imaging apparatus in accordance with a setting environment or use state. In addition, even if it is not possible to perform a given wireless setting method due to some factor, it is possible to perform wireless setting by using an alternate method.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-074863, filed Mar. 29, 2013, which is hereby incorporated by reference herein in its entirety.

What is claimed is:

1. A radiation imaging apparatus comprising:
   a radiation detection unit in which a plurality of photoelectric conversion elements configured to convert radiation into electric charges are arranged;
   a communication unit configured to output image data formed from electric charges read out from the photoelectric conversion elements;
   a setting unit configured to perform setting for connecting the communication unit wirelessly to an external apparatus, by executing processing based on a plurality of setting methods to obtain identification information to be used for communication with the external apparatus; and
   a control unit configured to select an infrared setting method from the plurality of setting methods in accordance with an input from an operation unit,
   wherein the control unit is configured to terminate the processing based on the infrared setting method and is configured to execute the processing based on WPS (Wi-Fi Protected Setup) setting method when the operation unit accepts a plurality of times of input within a predetermined time.

2. The apparatus according to claim 1, wherein the control unit is configured to select the setting method in accordance with the number of times of input accepted by the operation unit.

3. The apparatus according to claim 1, wherein after the operation unit accepts input once, the control unit is configured to execute processing for wireless setting by infrared as one of the plurality of setting methods.

4. The apparatus according to claim 3, wherein the control unit is configured to terminate the processing for wireless setting by infrared when no response to the processing is received within a predetermined time.

5. The apparatus according to claim 1, wherein the control unit is configured to terminate wireless setting based on the WPS (Wi-Fi Protected Setup) when a plurality of wireless relay apparatuses are detected by the processing for wireless setting based on the WPS (Wi-Fi Protected Setup), and
   when one wireless relay apparatus is detected by processing for wireless setting based on the WPS (Wi-Fi Protected Setup), the control unit is configured to execute processing for the wireless setting by communication via the detected wireless relay apparatus.

6. The apparatus according to claim 5, wherein when the operation unit accepts a plurality of times of input within a predetermined time and the wireless relay apparatus is not detected, the control unit is configured to search for a wireless relay apparatus in which an SSID (Service Set Identifier) including a portion common to an SSID set in the radiation imaging apparatus as one of the plurality of setting methods.

7. The apparatus according to claim 6, wherein when a plurality of wireless relay apparatuses are found, the control unit is configured to set a priority order of the plurality of wireless relay apparatuses in descending order of radio intensity.

8. The apparatus according to claim 7, wherein the control unit is configured to output a request signal for a connection acknowledgment to an imaging control apparatus of each network in accordance with the priority order,
   when a response signal to the request signal is received within a predetermined time, the control unit is configured to perform setting for connecting the communication unit to a network of an imaging control apparatus which has transmitted the response signal, and
   when the response signal is not received within the predetermined time, the control unit is configured to terminate processing.

9. The apparatus according to claim 1, wherein after the operation unit accepts input once, the control unit is configured to execute processing based on the plurality of setting methods, and is configured to perform setting for connecting the communication unit wirelessly to the external apparatus, by processing based on one setting method which has established communication with the external apparatus first.

10. The apparatus according to claim 1, wherein when communication with the external apparatus is established first, the control unit is configured to stop processing based on the plurality of setting methods except for processing based on the one setting method.

11. The apparatus according to claim 1, wherein the control unit is configured to perform setting for connecting the communication unit to a network formed by an relay apparatus for relaying information to the communication unit.

12. A radiation imaging system comprising:
a radiation imaging apparatus including a radiation detection unit in which a plurality of photoelectric conversion elements configured to convert radiation into electric charges are arranged and a communication unit configured to output image data formed from electric charges read out from the photoelectric conversion elements; and
an imaging control apparatus configured to control the radiation imaging apparatus,
wherein the radiation imaging apparatus comprises:
a setting unit configured to perform setting for connecting the communication unit wirelessly to an external apparatus, by executing processing based on a plurality of setting methods to obtain identification information to be used for communication with the external apparatus; and
a control unit configured to select an infrared setting method from the plurality of setting methods in accordance with an input from an operation unit,
wherein the control unit is configured to terminate the processing based on the infrared setting method and is configured to execute the processing based on WPS (Wi-Fi Protected Setup) setting method when the operation unit accepts a plurality of times of input within a predetermined time.

13. A non-transitory computer-readable storage medium storing a program for causing a computer to function as each unit of a radiation imaging apparatus that comprises a radiation detection unit in which a plurality of photoelectric conversion elements configured to convert radiation into electric charges are arranged, a communication unit configured to output image data formed from electric charges read out from the photoelectric conversion elements, a setting unit configured to perform setting for connecting the communication unit wirelessly to an external apparatus, by executing processing based on a plurality of setting methods to obtain identification information to be used for communication with the external apparatus, and a control unit configured to select an infrared setting method from the plurality of setting methods in accordance with an input from an operation unit,
wherein the control unit is configured to terminate the processing based on the infrared setting method and is configured to execute the processing based on WPS (Wi-Fi Protected Setup) setting method when the operation unit accepts a plurality of times of input within a predetermined time.

14. A radiation imaging apparatus comprising:
a radiation detection unit in which a plurality of photoelectric conversion elements configured to convert radiation into electric charges are arranged;
a communication unit configured to output image data formed from electric charges read out from the photoelectric conversion elements;
a setting unit configured to perform setting for connecting the communication unit wirelessly to an external apparatus, by executing processing based on a plurality of setting methods to obtain identification information to be used for communication with the external apparatus; and
a control unit configured to select a first setting method from the plurality of setting methods in accordance with an input from an operation unit,
wherein the control unit is configured to execute the processing based on a second setting method different from the first setting method, in a case in which the setting for connecting the communication unit wirelessly to the external apparatus by executing processing based on the first setting method is not completed, and
wherein when the operation unit accepts a plurality of times of input within a predetermined time, the control unit is configured to terminate the processing based on the first setting method, and is configured to execute the processing based on the second setting method.

15. The apparatus according to claim 14, wherein the first setting method is wireless setting by infrared communication having directivity.

16. The apparatus according to claim 14, wherein the second setting method is wireless setting by WPS (Wi-Fi Protected Setup).

17. The apparatus according to claim 14, wherein the control unit is configured to change the first setting method to the second setting method in a case in which the operation unit accepts an input within a predetermined time from a start time of wireless setting by the first setting method.

18. A radiation imaging method of a radiation imaging apparatus having a radiation detection unit in which a plurality of photoelectric conversion elements configured to convert radiation into electric charges are arranged, and a communication unit configured to output image data formed from electric charges read out from the photoelectric conversion elements, the method comprising:
a setting step of setting for connecting the communication unit wirelessly to an external apparatus, by executing processing based on a plurality of setting methods to obtain identification information to be used for communication with the external apparatus; and
a control step of selecting a first setting method from the plurality of setting methods in accordance with an input from an operation unit,
wherein in the control step the processing is executed based on a second setting method different from the first setting method, in a case in which the setting for connecting the communication unit wirelessly to the external apparatus by executing processing based on the first setting method is not completed, and
wherein when the operation unit accepts a plurality of times of input within a predetermined time, the control unit is configured to terminate the processing based on the first setting method, and is configured to execute the processing based on the second setting method.

19. A non-transitory computer-readable storage medium storing a program for causing a computer to function as each unit of a radiation imaging apparatus that comprises a radiation detection unit in which a plurality of photoelectric conversion elements configured to convert radiation into electric charges are arranged, a communication unit configured to output image data formed from electric charges read out from the photoelectric conversion elements, a setting unit configured to perform setting for connecting the communication unit wirelessly to an external apparatus, by executing processing based on a plurality of setting methods to obtain identification information to be used for communication with the external apparatus, and a control unit configured to select a first setting method from the plurality of setting methods in accordance with an input from an operation unit, wherein the control unit is configured to execute the processing based on a second setting method different from the first setting method, in a case that the setting for connecting the communication unit wirelessly to the external apparatus by executing processing based on the first setting method is not completed, and wherein when the operation unit accepts a plurality of times of input within a predetermined time, the control unit is configured to terminate the processing based on the first setting method, and is configured to execute the processing based on the second setting method.

* * * * *